United States Patent
Vincent et al.

(10) Patent No.: US 9,902,664 B2
(45) Date of Patent: Feb. 27, 2018

(54) PRODUCTION OF MONOALKYL AROMATIC COMPOUNDS

(71) Applicant: ExxonMobil Chemical Patents Inc., Baytown, TX (US)

(72) Inventors: Matthew J. Vincent, Kingwood, TX (US); Vijay Nanda, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 176 days.

(21) Appl. No.: 14/372,095

(22) PCT Filed: Dec. 13, 2012

(86) PCT No.: PCT/US2012/069562
§ 371 (c)(1),
(2) Date: Jul. 14, 2014

(87) PCT Pub. No.: WO2013/119318
PCT Pub. Date: Aug. 15, 2013

(65) Prior Publication Data
US 2015/0025286 A1    Jan. 22, 2015

Related U.S. Application Data

(60) Provisional application No. 61/596,427, filed on Feb. 8, 2012.

(30) Foreign Application Priority Data

Mar. 22, 2012    (EP) ..................................... 12160791

(51) Int. Cl.
*C07C 2/66*    (2006.01)
*B01J 8/04*    (2006.01)

(52) U.S. Cl.
CPC ............... *C07C 2/66* (2013.01); *B01J 8/0453* (2013.01); *B01J 8/0492* (2013.01); *B01J 8/0496* (2013.01);
(Continued)

(58) Field of Classification Search
CPC ........................................................ C07C 2/66
(Continued)

(56) References Cited

U.S. PATENT DOCUMENTS 4,870,222 A * 9/1989 Bakas ...................... B01J 29/22
585/323
5,336,821 A    8/1994 DeGraff et al.
(Continued)

FOREIGN PATENT DOCUMENTS

| WO | WO 2006/107471 | 10/2006 |
| WO | WO 2008/055116 | 5/2008 |
| WO | WO 2011/123302 | 10/2011 |

*Primary Examiner* — Thuan D Dang
(74) *Attorney, Agent, or Firm* — Darryl M. Tyus (57) ABSTRACT

The present disclosure relates to a process for production of a monoalkyl aromatic compound by alkylation of alkylatable aromatic compounds with an alkylating agent in a reactor comprising at least a first and a second series-connected alkylation reaction zones and a cooler disposed between the first and the second series-connected alkylation reaction zones. The process comprising a step of cooling at least a portion of an effluent withdrawn from the first alkylation reaction zone before being introduced into the second alkylation reaction zone.

8 Claims, 4 Drawing Sheets

(52) U.S. Cl.
CPC ............... *B01J 2208/00168* (2013.01); *B01J 2208/00256* (2013.01); *B01J 2208/00274* (2013.01); *C07C 2529/08* (2013.01); *C07C 2529/18* (2013.01); *C07C 2529/70* (2013.01); *Y02P 20/582* (2015.11)

(58) Field of Classification Search
USPC ...................................... 585/448, 449, 467
See application file for complete search history.

(56) References Cited

U.S. PATENT DOCUMENTS

| | | |
|---|---|---|
| 5,900,518 A | 5/1999 | Merrill et al. |
| 6,008,422 A | 12/1999 | Schultz et al. |
| 6,835,862 B1 | 12/2004 | Gajda et al. |
| 6,995,295 B2 | 2/2006 | Clark et al. |
| 7,645,913 B2 | 1/2010 | Clark et al. |
| 2006/0224031 A1* | 10/2006 | Jan ........................ B01J 29/06 585/467 |
| 2007/0265481 A1 | 11/2007 | Clark et al. |
| 2008/0021252 A1 | 1/2008 | Schwint |

\* cited by examiner

PRODUCTION OF MONOALKYL AROMATIC COMPOUNDS

CROSS REFERENCE TO RELATION APPLICATIONS

This application is a 371 National Stage Application of International Application No. PCT/US2012/069562 filed Dec. 13, 2012, which claims the benefit of and priority to U.S. Provisional Application Ser. No. 61/596,427 filed Feb. 8, 2012, and European Application No. 12160791.5, filed Mar. 22, 2012, the disclosures of which are fully incorporated herein by reference in their entireties.

FIELD

The present disclosure relates to a process for production of a monoalkyl aromatic compound, in particular cumene, and a reactor suitable for the process.

BACKGROUND

Alkyl aromatic compounds, such as cumene and ethylbenzene, are often produced by reaction of alkylating alkylatable aromatic compounds with an alkylating agent. For example, cumene (or isopropylbenzene) is industrially produced by alkylation of benzene with propylene. Alkylation is an exothermic reaction. Cooling is needed to manage the temperature increase in the reactor, in the existing cumene production technology, the total reactor effluent containing cumene is cooled, recycled and re-introduced into the first alkylation reaction zone to manage temperature rise from the exothermic reaction of benzene with propylene. The recycled cumene, however, provides an opportunity for it to be further alkylated to undesired byproducts, for example, di-isopropylbenzene and tri-isopropylbenzene.

Many attempts have been made in the art to manage the temperature rise during the alkylation of benzene with $C_2$ to $C_4$ olefins.

U.S. Pat. No. 6,008,422 discloses a process for producing alkylaromatics using a multibed alkylation reaction zone. The alkylation reaction zone effluent is divided into three portions, the first being recirculated to the inlet of the alkylation reaction zone, the second being cooled and recirculated to one or more other beds in the alkylation reaction zone, and third being passed to a product recovery zone where the alkylaromatic compound is recovered.

U.S. Patent Application Publication No. 2008-021252 discloses a process for the production of alkylated aromatic compounds, in which aromatic compounds from each of at least the first and second catalytic alkylation reaction zones are contacted with a cooling means for re-condensing at least a portion of the aromatic compounds vaporized from the exothermic heat of reaction of the alkylation process.

U.S. Pat. No. 5,336,821 discloses a process for the alkylation of aromatic hydrocarbons such as cumene and ethylbenzene, in which a portion of the effluent stream from an alkylation reactor passes through an indirect heat exchanger to transfer heat to a flashed stream containing the product aromatic hydrocarbons, and the heat exchanger recovers the exothermic heat of the reaction from the effluent stream for use elsewhere in the process.

U.S. Pat. No. 6,835,862 discloses a process for the alkylation of aromatics with olefins using a solid catalyst, wherein the olefin ratio and/or the maximum olefin concentration in the alkylation catalyst bed is maintained less than an upper limit.

U.S. Pat. No. 5,900,518 discloses a process for heat integration alkylation/transalkylation process, in which the alkylation effluent passes into the first separation zone which is operated to produce a lower boiling fraction comprising the aromatic substrate, which may be recycled to the alkylation reaction zone, and a higher boiling fraction comprising a mixture of monoalkylated aromatics and polyalkylated aromatics.

U.S. Patent Application Publication No. 2007-0265481 describes a process for producing an alkylaromatic compound in a multistage reaction system comprising at least first and second series-connected alkylation reaction zones each containing an alkylation catalyst. A first feed comprising an alkylatable aromatic compound and a second feed comprising an alkene and one or more alkanes are introduced into said first alkylation reaction zone. The first alkylation reaction zone is operated under conditions of temperature and pressure effective to cause alkylation of the aromatic compound with the alkene in the presence of the alkylation catalyst, the temperature and pressure being such that the aromatic compound is partly in the vapor phase and partly in the liquid phase. An effluent comprising the alkylaromatic compound, unreacted alkylatable aromatic compound, any unreacted alkene and the alkane is withdrawn from the first alkylation reaction zone and then supplied to the second alkylation reaction zone without removal of the alkane. The operating conditions in each of said first and second reaction zones are such that the ratio of the volume of liquid to the volume of vapor in each zone is from about 0.1 to about 10.

U.S. Pat. No. 6,995,295 discloses a process for producing an alkylaromatic compound by reacting an alkylatable aromatic compound with a feed comprising an alkene and an alkane in a multistage reaction system comprising at least first and second series-connected alkylation reaction zones each containing an alkylation catalyst. At least the first alkylation reaction zone is operated under conditions of temperature and pressure effective to cause alkylation of the aromatic compound with the alkene in the presence of the alkylation catalyst, the temperature and pressure being such that the aromatic compound is partly in the vapor phase and partly in the liquid phase. An effluent comprising the alkylaromatic compound, unreacted alkylatable aromatic compound, any unreacted alkene and the alkane is withdrawn from the first alkylation reaction zone and at least part of the alkane is removed from the effluent to produce an alkane-depleted effluent. The alkane-depleted effluent is then supplied to the second alkylation reaction zone.

U.S. Pat. No. 7,645,913 discloses a process for producing an alkylaromatic compound in a multistage reaction system comprising at least first and second series-connected alkylation reaction zones. In this process, the alkylation catalyst in the first alkylation reaction zone, which may be a reactive guard bed, has more acid sites per unit volume of catalyst than the alkylation catalyst in the second reaction zone.

Figure 1:
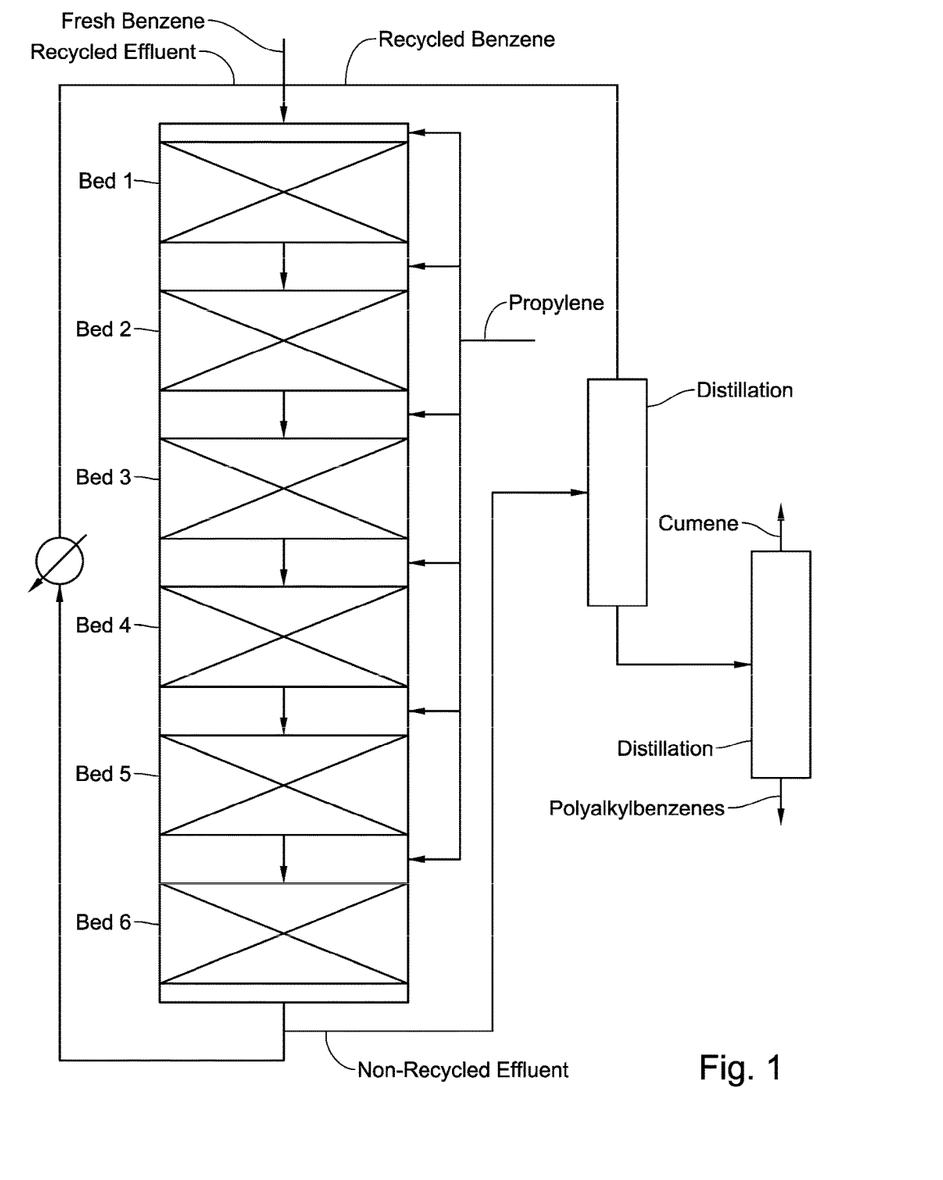
FIG. 1 shows an illustrative diagram of one embodiment of the process in the prior art.
Figure 2:
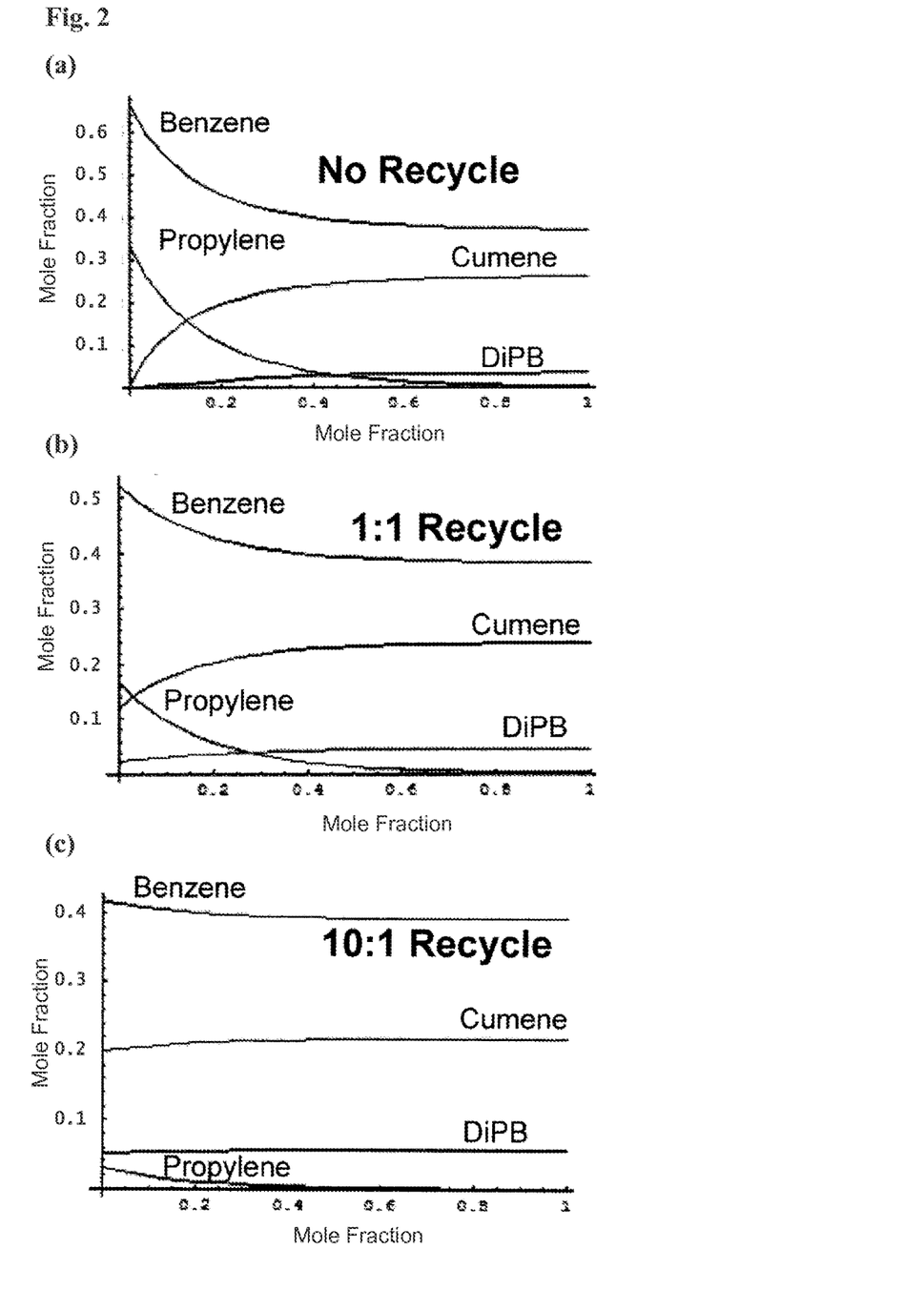
FIG. 2(a) to (c) shows the relationship for the first bed between the recycle ratio and formation of by-products in an existing process for production of cumene as shown in FIG. 1.
Figure 3:
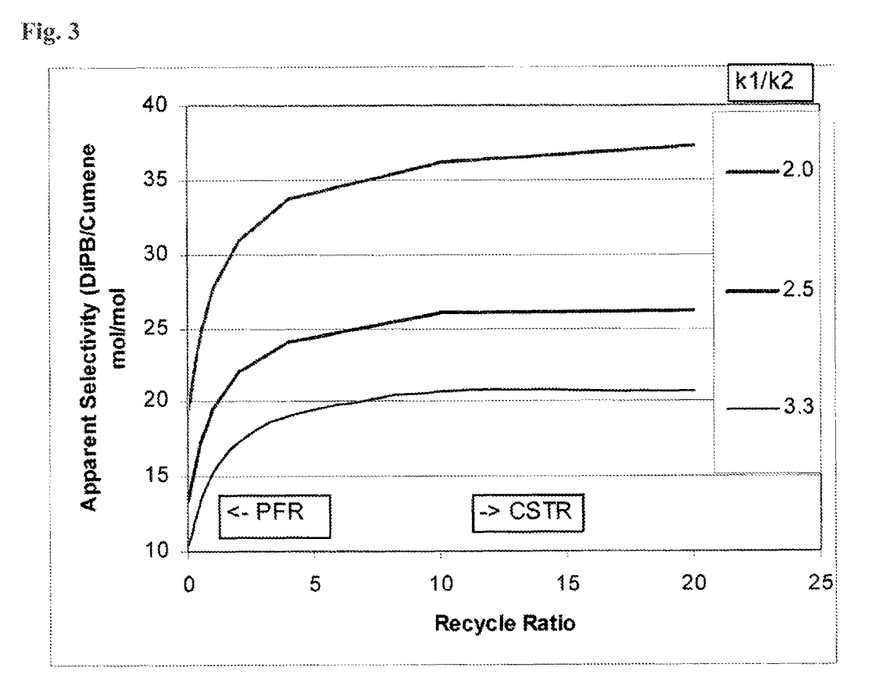
FIG. 3 shows the relationship between recycle ratio and selectivity for the first bed in an existing process for production of emetic as shown in FIG. 1.

In a process for the production of monoalkyl aromatic compounds, for example, cumene by alkylation of benzene with propylene, the byproduct, di-isopropyl benzene is formed by the subsequent alkylation of cumene:

However the process is exothermic and usually comprises a step of recycling at least a portion of the reactor effluent to cooler and to the reactor inlet to dilute the feed and reduce the temperature rise from alkylation. (See FIG. 1.) A recycle ratio is defined herein as a weight ratio of the recycled portion of the reactor effluent to the non-recycled portion of the reactor effluent. In such a process, the inventor realizes that, as the recycle ratio increases, the average concentration of monoalkyl aromatic compound at the reactor inlet increases, thus providing opportunity for further reaction of the monoalkyl compounds to polyalkyl compounds. FIG. 2(a)-(c) shows in units of mole fraction that as the recycle ratio is increased, the formation of the diisopropylbenzene (DiPB) byproduct also increases. As a result, the undesirable byproduct selectivity of diisopropylbenzene (defined as the ratio of dialkylbenzene divided by cumene) increases with increasing recycle ratio, as shown in FIG. 3. Thus, FIG. 3 indicates that byproduct selectivity can be lowered by operating at lower recycle ratios.

Therefore, there is a need to devise a process for production of monoalkyl aromatic compounds by alkylation of alkylatable aromatic compounds with an alkylating agent with high selectivity to desired monoalkyl aromatic and low formation of byproducts such as polyalkyl aromatic compounds.

SUMMARY OF THE INVENTION

In one embodiment the present disclosure provides a process for production of a monoalkyl aromatic compound in a reactor having at least a first and a second series-connected alkylation reaction zones, each reaction zone having an alkylation catalyst, the process comprising the steps of:

a) introducing a first feed comprising an alkylatable aromatic compound and a second feed comprising an alkylating agent into said first alkylation reaction zone;

b) operating said first alkylation reaction zone under at least partly liquid phase conditions sufficient to cause alkylation of said alkylatable aromatic compound by said alkylating agent in the presence of said alkylation catalyst to produce a first effluent comprising said monoalkyl aromatic compound and unreacted alkylatable aromatic compound;

c) withdrawing said first effluent from said first reaction zone;

d) cooling at least a portion of said first effluent to form a cooled first effluent;

e) supplying said cooled first effluent and the rest of said first effluent, and optionally a third feed comprising additional said alkylating agent to said second alkylation reaction zone; and f) operating said second alkylation reaction zone under at least partly liquid phase conditions sufficient to cause alkylation of said unreacted alkylatable aromatic compound by said alkylating agent in the presence of said alkylation catalyst to produce a second effluent comprising additional said monoalkyl aromatic compound and unreacted alkylatable aromatic compound.

In one or more embodiments, the step di comprises cooling at least 50% by weight of the effluent. While in one or more other embodiments, the step d) comprises cooling all of the effluent, and step (e) comprises supplying all of said cooled first effluent to said second alkylation reaction zone.

In some embodiments, the process further comprises the steps of:

g) withdrawing a reactor effluent which comprises at least said first and second effluents from said reactor; and h) recycling a portion of said effluent to said first reaction zone or said second reaction zone for alkylation of said unreacted alkylatable aromatic compound, wherein the ratio by weight of the recycled portion to non-recycled portion of said reactor effluent is in the range of greater than or equal to about zero to less than or equal to about 5.

In other embodiments, the process further comprises the steps of:

g) withdrawing a reactor effluent which comprises at least said first and second effluents from said reactor; and h) supplying all of said reactor effluent to a separation zone to separate at least a portion of said unreacted alkylatable aromatic compound from said reactor effluent; and i) recycling said portion of said unreacted alkylatable aromatic compound to said first alkylation reaction zone or said second alkylation reaction zone.

In another aspect, the present disclosure provides a reactor for production of a monoalkyl aromatic compound by alkylating an alkylatable aromatic compound with an alkylating agent comprising:

a) at least a first and a second alkylation reaction zones; and b) a cooler disposed between said first and second alkylation reaction zone.

In one or more embodiments of the present disclosure, each of the first and second alkylation reaction zones of the reactor can each independently comprise one, two, three or four series-connected alkylation catalyst beds, more preferably one, or two series-connected alkylation catalyst beds.

In the process of the present disclosure, by arranging an internal cooling step between alkylation reaction zones in the same reactor, the temperature of the alkylation reaction zones is controlled to the optimal range. Not to be bound by any theories, it is believed under such conditions most of the aromatic compounds are reacted with alkylating agent to form the desired monoalkyl aromatic compound and formation of by-products decreases accordingly. This reduces the burden of separation in the downstream and thereby enables reduction or even elimination of recycle of effluent back to the reactor entrance, which further increases the selectivity to the desired monoalkyl aromatic compounds.

With reduced formation of by-products, when reducing or even eliminating recycle of effluent, the opportunity for further alkylation of monoalkyl aromatic compound to polyalkyl aromatic compound is still reduced, and therefore formation of by-products is decreased from another aspect, which forms a beneficial cycle.

DETAILED DESCRIPTION OF THE INVENTION

Now each of the inventions will be described in greater detail, including specific embodiments, versions and examples, but the inventions are not limited to these embodiments, versions or examples, which are included to enable a person having ordinary skill in the art to make and use the inventions, when the information in this patent is combined with available information and technology.

The present disclosure provides a reactor and a process for producing monoalkyl aromatic compound by alkylation of an alkylatable aromatic compound under at least partly liquid phase with an alkylating agent. Although in the following discussion the production of cumene by alkylation of benzene with propylene will be mainly described, the present disclosure can be equally applicable to the production of other monoalkyl aromatic compounds, for example, ethylbenzene and sec-butylbenzene.

In the present disclosure, a "monoalkyl aromatic compound" or "monoalkylated aromatic compound" has one more alkyl group corresponding to the olefin than the feed aromatic, for example, cumene; and a "polyalkyl aromatic compound" or "polyalkylated aromatic compound" has two, three or more alkyl groups corresponding to the olefin than the feed aromatic, for example, di-isopropylbenzene and tri-isopropylbenzene.

The present disclosure in one aspect provides a process for production of a monoalkyl aromatic compound in a reactor having at least a first and a second series-connected alkylation reaction zones, each reaction zone having an alkylation catalyst, the process comprising the steps of:

a) introducing a first feed comprising an alkylatable aromatic compound and a second feed comprising an alkylating agent into said first alkylation reaction zone;

b) operating said first alkylation reaction zone under at least partly liquid phase conditions sufficient to cause alkylation of said alkylatable aromatic compound by said alkylating agent in the presence of said alkylation catalyst to produce a first effluent comprising said monoalkyl aromatic compound and unreacted alkylatable aromatic compound;

c) withdrawing said first effluent from said first reaction zone;

d) cooling at least a portion of said first effluent to form a cooled first effluent;

e) supplying said cooled first effluent and the rest of said first effluent, and optionally a third feed comprising additional said alkylating agent to said second alkylation reaction zone; and f) operating said second alkylation reaction zone under at least partly liquid phase conditions sufficient to cause alkylation of said unreacted alkylatable aromatic compound by said alkylating agent in the presence of said alkylation catalyst to produce a second effluent comprising additional said monoalkyl aromatic compound and unreacted alkylatable aromatic compound.

Reactants

The reactants used in the process of the disclosure include an alkylatable aromatic compound and an alkylating agent.

The term "alkylatable aromatic compound" herein is to be understood in accordance with its art-recognized scope which includes alkyl-substituted and unsubstituted mono- and polynuclear aromatic compounds. Compounds of an aromatic character which possess a heteroatom are also useful provided they do not rapidly (in less than 1 day) deactivate the catalyst by poisoning the catalyst under the reaction conditions selected.

Substituted aromatic compounds, which may be alkylated herein, must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene (or cumene), normal propylbenzene, alpha-methylnaphthalene, ethylbenzene, mesitylene, durene, cumene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$.

Reformate or cut thereof containing substantial quantities of benzene (>1%), toluene and/or xylene constitutes a particularly useful feed for the alkylation process of this disclosure.

Suitable alkylating agents useful in the process of this disclosure include alkenes, such as ethylene, propylene, 1-butene and 2-butene, preferably propylene.

Preferably, the reactants in the process of the disclosure are benzene and propylene and the desired reaction product is cumene.

Alkylation Catalysts

In the process of the present disclosure, the first and second alkylation reaction zones contain an alkylation catalyst. The alkylation catalyst in such reaction zones may be the same or different. In the preferred embodiments, the alkylation catalyst is contained in an alkylation catalyst bed contained in the alkylation reaction zones. In one embodiment, an alkylation catalyst contained in the alkylation reaction zones or the alkylation catalyst beds in the alkylation reaction zones comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477, ZSM-23 is described in U.S. Pat. No. 4,076,842. ZSM-35 is described in U.S. Pat. No. 4,016,245. ZSM-48 is more particularly described in U.S. Pat. No. 4,234,231.

In another embodiment, the alkylation catalyst contained in the alkylation reaction zones or the alkylation catalyst beds in the alkylation reaction zones comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof, and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), and MCM-56 (described in U.S. Pat. No. 5,362,697) and mixtures thereof.

The alkylation catalyst may be UZM-8 (described in U.S. Pat. No. 6,756,030) or UZM-8HS (described in U.S. Pat. No. 7,713,513), and mixtures thereof.

In a further embodiment, the alkylation catalyst contained in the alkylation reaction zones or the alkylation catalyst beds in the alkylation reaction zones comprises one or more large pore molecular sieves having a Constraint Index less than 2.

Suitable large pore molecular sieves include zeolite beta, faujasite, zeolite Y, Ultrastable Y (USY), Dealuminized Y (Deal Y), Rare earth exchanged Y (REY), mordenite, TEA-mordenite, ZSM-3, ZSM-4, ZSM-8, ZSM-20, and combinations thereof. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069 and Re. No. 28,341. Low sodium Ultrastable Y molecular sieve (USY) is described in U.S. Pat. Nos. 3,293,192 and 3,449,070. Dealumninized Y zeolite (Deal Y) may be prepared by the method found in U.S. Pat. No. 3,442,795. Zeolite Ultrahydrophobic, Y (UHP-Y) is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferred molecular sieves for use in the present process comprise ZSM-5 zeolite beta, zeolite Y, Ultrastable Y (USY), and zeolites of the MCM-22 family.

The above molecular sieves may be used as the alkylation catalyst in the process of the disclosure without any hinder or matrix, i.e., in so-called self-bound form. Alternatively, the molecular sieve may be combined with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active, may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

Generally, the alkylatable aromatic compound and the alkylating agent supplied to the present process will contain some level of reactive impurities, such as nitrogen compounds, which are small enough to enter the pores of the alkylation catalyst and thereby poison the catalyst. Moreover, it is normal to supply all alkylatable aromatic compounds to the first alkylation reaction zone, but to divide the alkene feed between the alkylation catalyst beds. Thus, the catalyst in the first alkylation reaction zone, especially the first alkylation catalyst bed is more likely to be poisoned by impurities. Thus, to reduce the frequency with which the catalyst in the first alkylation reaction zone or in the first alkylation catalyst bed must be removed for replacement, regeneration or reactivation, the present process preferably employs in the first alkylation catalyst bed of the first alkylation reaction zone an alkylation catalyst having a greater number of acid sites per unit mass of the catalyst than the others. Apart from the difference in the number of acid sites per unit mass of the catalyst, the first and second alkylation catalysts can employ the same or different zeolite materials.

Alkylation Conditions

In the process of the present disclosure, the alkylation reaction in each of series-connected alkylation reaction zones takes place under at least partly liquid conditions which may be maintained throughout such zones. Each alkylation reaction zone is operated under conditions effective not only to cause alkylation of the alkylatable aromatic compound with the alkylating agent in the presence of the alkylation catalyst, but also to result in the aromatic compound being at least partly in the liquid phase. More particularly, the operating conditions in each alkylation reaction zone are controlled such that the alkylatable aromatic compound is either in the complete liquid phase or in the partly liquid phase. In the present disclosure, the expression "in the complete liquid phase" includes herein a phase containing less than 1% by volume of vapor phase based on the total volume of liquid phase and vapor phase.

Except that the alkylatable aromatic compound is in the complete liquid phase, the operating conditions in each alkylation reaction zone may be in the partly liquid phase. In one embodiment, a ratio of the volume of vapor to the sum of volumes of vapor and liquid in each of the alkylation catalyst bed in each alkylation reaction zone is greater than 0.01 to less than about 0.1, less than about 0.05, less than about 0.03, or less than about 0.02. In determining the vapor to liquid volume ratio in a given alkylation reaction zone, the total volume of all the reactants in the vapor phase in the alkylation catalyst bed in the alkylation reaction zone is divided by the total volume of all the reactants in the vapor and liquid phase in the alkylation catalyst bed in the alkylation reaction zone.

It is to be appreciated that maintaining the alkylatable aromatic compound in the complete liquid phase or in the partly liquid phase is a function of many variables, including temperature, pressure, feed composition, the weight ratio of aromatics to alkylating agent, and the number of interstage feed injection points (feed distribution among the alkylation catalyst beds). Each of these variables must be understood and monitored in order to maintain the ratio of the volume of liquid to the volume of vapor at the desired level.

In the process of the present disclosure, the alkylation reaction is operated in each alkylation reaction zone comprising alkylation catalyst bed(s), and effluent withdrawn from an alkylation reaction zone generally comprises desired monoalkyl aromatic compound, polyalkyl aromatic compounds, and unreacted alkylatable aromatic compound and unreacted alkylating agent. An effluent withdrawn from first reaction zone is called herein the first effluent, and an effluent withdrawn from the second reaction zone is called herein the second effluent, and an effluent withdrawn from a finishing reaction zone of the reactor is called herein a reactor effluent. Conventionally most of the alkylating agent (overall conversion is expected to be 98-99.99+%), for example, alkene is converted and accordingly as an effluent withdrawn from an upstream alkylation reaction zone passes into a downstream, subsequent alkylation reaction zone, a new feed comprising an additional alkylating agent is fed to the downstream, subsequent alkylation reaction zone.

In the process of the present disclosure, the first effluent withdrawn from the first alkylation reaction zone is subjected to a cooling step before re-injection to the second alkylation reaction zone so that the temperature of the effluent is controlled to the optimal range, which varies from different alkylation reactions, before alkylation occurs in the second alkylation reaction zone. Accordingly the byproduct formation, for example, diisopropylbenzene and tripropylbenzene, is significantly decreased in the second alkylation reaction zone, and a reactor effluent withdrawn from the reactor (or the last alkylation reaction zone of the reactor) comprises decreased byproducts. In one preferred embodiment, only a portion of the first effluent is cooled, and the cooled portion of the first effluent and the rest are combined and introduced to the second alkylation reaction zone. In another preferred embodiment, all the first effluent is cooled and then supplied to the second alkylation reaction zone. In the cooling step, the cooler can be any coolers or heat exchangers known in the art.

In the process of the present disclosure, a reactor effluent withdrawn from the alkylation reactor could be divided into two streams, i.e., a recycled portion and a non-recycled portion. A recycle ratio is defined herein as a ratio by weight of the recycled portion to the non-recycled portion. In some embodiments, the recycle ratio is greater than zero to less than about 5, about 4, about 3, about 2.5, about 2, about 1.5, or about 1. In other embodiments, the recycle ratio could be zero, that is, all effluent could be subjected to the separation scheme downstream of the alkylation reactor.

The recycled portion of the reactor effluent is recycled to a reactor as a feed of starting materials. In some embodiments, the recycled portion of the reactor effluent can be recycled to the first alkylation reaction zone, the second alkylation reaction zone, or both of the reactor from which the effluent is withdrawn. In some other embodiments, the recycled portion of the reactor effluent may be recycled to a separate reactor upstream or downstream of the reactor from which the effluent is withdrawn. The separate reactor would also contain alkylation catalyst, which could be the same or different from the alkylation catalyst used in the reactor and could be operated under vapor phase, liquid phase or mixed phase alkylation conditions.

The non-recycled portion of the effluent is subjected to separation of monoalkyl aromatic compound in which the unreacted alkylating agent, unreacted alkylatable aromatic compound, and desired monoalkyl aromatic compound are serially separated. The remaining polyalkyl aromatic compounds could be then fed to a transalkylation reactor, which is normally separate from the alkylation reactor, where additional monoalkylated product is produced by transalkylation of the polyalkyl aromatic compounds with additional aromatic compounds.

In the process of the present disclosure, the formation of by-products decreases, and that increases or maximizes the capacity of separation of desired products in the downstream.

In addition to and upstream of the alkylation reactor, the reaction system may also include a pre-reactor containing a by-passable reactive guard bed which is separate from the reactor of the present disclosure. The reactive guard bed in the pre-reactor is also loaded with alkylation catalyst, which may be the same or different from the catalyst used in the reactor of the present disclosure, and is maintained under ambient or up to alkylation conditions. The alkylatable aromatic compound and alkylating agent feeds are passed through the reactive guard bed prior to entry into the first alkylation reaction zone. The reactive guard bed not only serves to effect the desired alkylation reaction but also to remove any reactive impurities in the feeds, such as nitrogen compounds, which could otherwise poison the remainder of the alkylation catalyst. The catalyst in the guard bed is therefore subject to more frequent regeneration and/or replacement than the remainder of the alkylation catalyst and hence the guard bed is normally provided with a by-pass circuit so that the alkylation feeds may be fed directly to the series-connected alkylation reaction zones when the guard bed is out of service. The reactive guard bed may operate in all liquid phase or mixed phase in co-current up-flow or down-flow operation. The reactive guard bed may also be included in the reactor of the present disclosure upstream of the first alkylation reaction zone of the reactor.

Particular conditions for carrying out the liquid or mixed phase alkylation of benzene with ethylene to produce ethylbenzene may include a temperature of from about 120° C. to about 270° C., a pressure of about 675 KPa to about 8300 KPa, a WHSV based on ethylene of from about 0.1 to about 10 hr$^{-1}$, and a molar ratio of benzene to ethylene from about 1 to about 10.

Particular conditions for carrying out the liquid or mixed phase alkylation of benzene with propylene to produce cumene may include temperature of about 75° C. to about 250° C., a pressure of about 675 KPa to about 5000 KPa, a WHSV based on propylene of from about 0.1 to about 10 hr$^{-1}$, and a molar ratio of benzene to propylene from about 1 to about 10.

Particular conditions for carrying out the liquid or mixed phase alkylation of benzene with 1-butene and/or 2-butene to produce sec-butylbenzene may include a temperature of about 75° C. to about 250° C., a pressure of about 355 kPa to about 4000 KPa, a WHSV based on butene of from about 0.1 to about 10 hr$^{-1}$ and a molar ratio of benzene to butene from about 1.0 to about 5.0.

Where the alkylation system includes a reactive guard bed, this may be operated under liquid phase conditions or mixed liquid/vapor phase conditions, but is preferably operated under liquid phase conditions. In the case of ethylbenzene production, the guard bed will preferably operate at a temperature between about 20° C. and about 270° C. to 285° C. and a pressure between about 675 to about 8300 kPa. In the case of cumene production, the guard bed will preferably operate at a temperature from about 25° C. to 180° C. and pressure from about 675 to 4000 kPa. In the case of sec-butylbenzene production, the guard bed will preferably operate at a temperature from about 50° C. to 250° C. and pressure from about 445 to 3550 kPa. The molar ratio of alkylatable aromatic to alkylating agent is in the range of 20:1 to 100:1. The weight hourly space velocity based on alkylation agent is in the range of 0.1 to 10 hr$^{-1}$. The alkylating agent may contain less than or equal to 0.1 wt. % alkene (i.e., including, but not limited to methane, ethane or propane) based on the weight of the total feed to the reactive guard bed.

Transalkylation

The monoalkyl aromatic compound, the unreacted alkylating agent, unreacted alkylatable aromatic compound, desired monoalkyl aromatic compound, and polyalkylated aromatic compound are separated. The polyalkylated aromatic compounds can be then fed to a transalkylation reactor, which is normally separate from the alkylation reactor, where additional monoalkylated product is produced by reacting the polyalkylated species with additional aromatic compound in the presence of a transalkylation catalyst. Typically, the transalkylation reactor is operated under conditions such that the polyalkylated aromatic compounds and the alkylatable aromatic compound are at least predominantly in the liquid phase.

For example, suitable conditions for carrying out the liquid phase transalkylation of benzene with polyethylbenzenes may include a temperature of from about 150° C. to about 260° C., a pressure of about 7000 KPa or less, a WHSV based on the weight of the total liquid feed to the alkylation reaction zone of from about 0.5 hr$^{-1}$ to about 100 hr$^{-1}$ and a molar ratio of benzene to polyethylbenzenes of from about 1:1 to about 30:1. Particular conditions for carrying out the liquid phase transalkylation of benzene with polypropylbenzene may include a temperature of from about 150° C. to about 300° C., a pressure of about 5500 KPa or less, a WHSV based on the weight of the total liquid feed to the alkylation reaction zone of from about 0.1 hr$^{-1}$ to about 20.0 hr$^{-1}$ and a molar ratio of benzene to polypropylbenzene of from about 1.0 to about 10.0. Particular conditions for carrying out the liquid phase transalkylation of benzene with polybutylbenzene may include a temperature of from about 100° C. to about 300° C., a pressure of about 1000 KPa to about 7000 KPa, a WHSV of 1 hr$^{-1}$ to 50 hr$^{-1}$ on total feed, and a benzene to polybutylbenzene weight ratio of 1 to 10.

The transalkylation catalyst can comprise one or more of any of the molecular sieves discussed above in relation to the vapor phase alkylation system and can be used with or without a binder or matrix. Generally, however, the transalkylation catalyst is selected from zeolite beta, faujasite, zeolite Y, Ultrastable Y (USY), Dealuminized Y (Deal Y), Rare earth exchanged Y (REY), Ultrahydrophobic Y (UHP-Y), mordenite, TEA-mordenite, ZSM-3, ZSM-4, ZSM-18, ZSM-20, and combinations thereof.

Reactor

The present disclosure further provides a reactor suitable to process the present disclosure. The reactor contains at least two alkylation reaction zones, each reaction zone comprising at least one alkylation catalyst bed having an alkylation catalyst. In one embodiment, the reactor comprises two alkylation reaction zones, and each reaction zone contains one alkylation catalyst bed having an alkylation catalyst. In another embodiment, the reactor comprises two alkylation reaction zones, and each reaction zone contains two alkylation catalyst beds having an alkylation catalyst. In one embodiment, the reactor comprises three alkylation reaction zones, and each reaction zone contains one alkylation catalyst bed having an alkylation catalyst. In another embodiment, the reactor comprises three alkylation reaction zones, and each reaction zone contains two alkylation catalyst beds having an alkylation catalyst. In addition, in the reactor of present disclosure, the amount of alkylation catalyst beds in each alkylation reaction zone may be different. For example, in one embodiment, the first alkylation reaction zone comprises two alkylation catalyst beds, and the second alkylation reaction zone comprises one alkylation catalyst bed. In another embodiment, the first alkylation reaction zone comprises one alkylation catalyst bed, and the second alkylation reaction zone comprises two alkylation catalyst beds.

The reactor of present disclosure comprises a cooler (heat exchanger) arranged between the alkylation reaction zones for removing heat of effluent output from reaction zones. Any known heat exchangers in the art can be suitable to the reactor of present disclosure as long as they can be mounted into the reactor. For example, cooling coils or tube bundles could be disposed within the reactor between alkylation reaction zones. On the other hand, for purpose of carrying out the process of present invention, the heat exchangers can be mounted outside of the reactor.

The reactor of the present disclosure comprises means adapted to connect to said cooler and said second alkylation reaction zone, said means for controlling the temperature of said second alkylation reaction zone to maintain at least partial liquid phase conditions sufficient to cause alkylation of said unreacted benzene by said additional propylene in the presence of said alkylation catalyst to produce a second effluent comprising additional said cumene and unreacted benzene. Alternatively, said means be used for controlling the temperature of said second alkylation reaction zone to al temperature above, similar or below the temperature of said first feed stream which comprises benzene.

According to the present disclosure, the number of alkylation reactors, alkylation reaction zones, and alkylation catalyst beds may have different combinations. A person skilled in the art would know the preferable arrangement for any specific production of monoalkyl aromatic compound in view of reduction of temperature rise to control the temperature to the optimal range, cost saving and reduction of energy consumption. For example, in one or more embodiments, the number of the reactor can be three, two, or one, the number of alkylation reaction zones in the reactor can be six, five, four, three, or two, and the number of alkylation catalyst beds in each alkylation reaction zone in the reactor can be four, three, two or one.

In the reactor of the present disclosure, the alkylation reaction zones may contain one or more alkylation catalyst beds; the alkylation reaction is operated in each alkylation catalyst bed of the alkylation reaction zones. Therefore in this disclosure, unless otherwise specified, any expressions/phrases same as or similar to "alkylation in the alkylation reaction zone" shall be referred to alkylation in the alkylation catalyst bed(s) in the alkylation reaction zone; any expressions/phrases same as or similar to "effluent withdrawn from the alkylation reaction zone" shall be referred to the effluent withdrawn from alkylation catalyst bed, or the last (the most downstream) alkylation catalyst bed if more than one alkylation catalyst bed is contained in the alkylation reaction zone; and any expression/phases same as or similar to "feed to the alkylation reaction zone" shall be referred to feeding the alkylation catalyst bed, or the first (the most upstream) alkylation catalyst bed if more than one alkylation catalyst bed is contained in the alkylation reaction zone. In an alkylation reaction zone containing more than one alkylation catalyst bed, an effluent withdrawn from an upstream alkylation catalyst bed directly passes to a downstream alkylation catalyst bed for further alkylation.

The reactor of the present disclosure is suitable for the process of present disclosure; however, the process of the present disclosure is not limited to the present reactor. Any reactor comprising at least first or second alkylation reaction zones can be used in the process of present invention.

Figure 4:
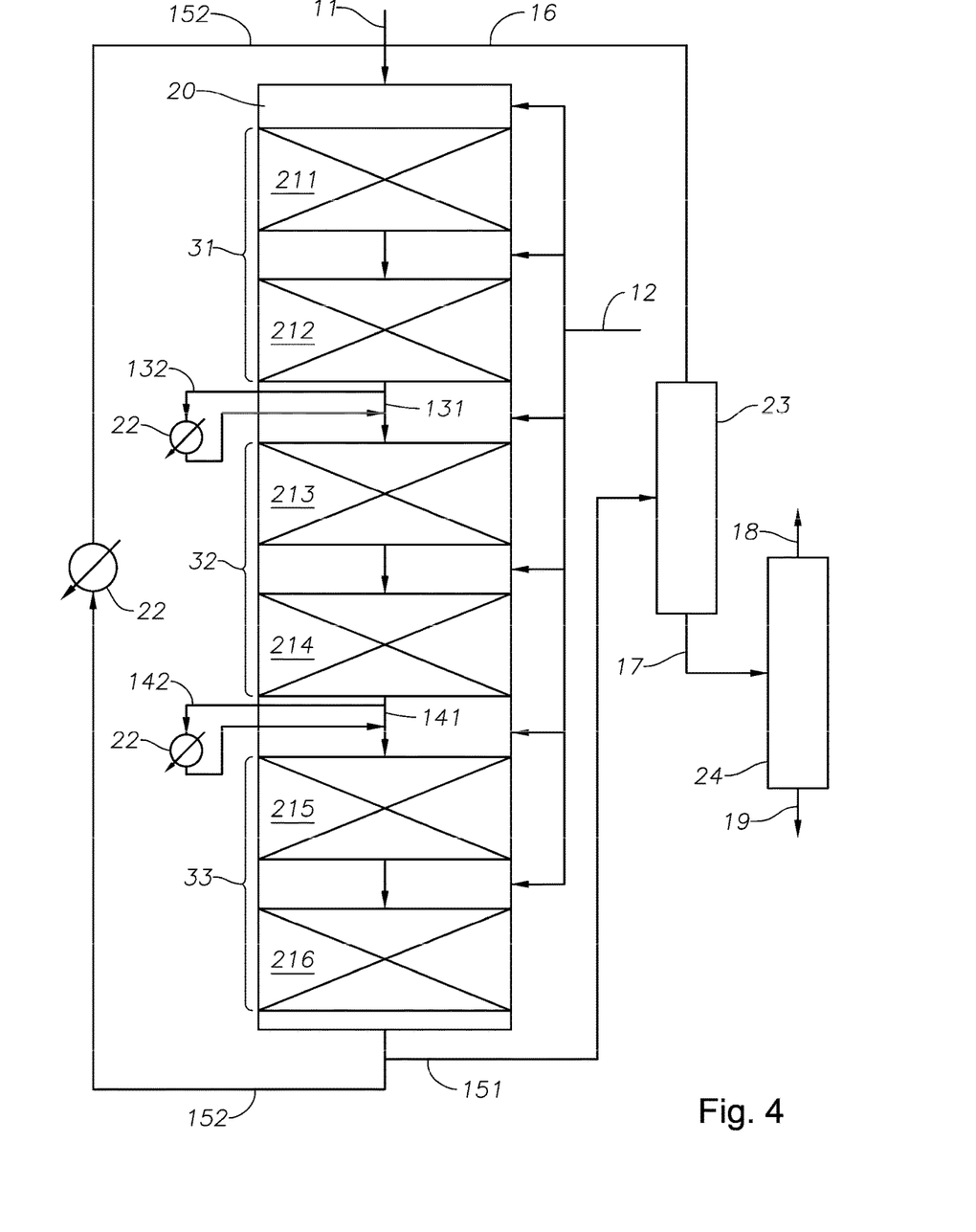
FIG. 4 shows an illustrative diagram of one specific embodiment of the inventive process of present disclosure.

Now, a more detailed description about the process will be explained with reference to the FIG. 4, which shows a preferred embodiment of the present process. For purpose of easy understanding, the alkylatable aromatic compound in this embodiment is benzene and the alkylating agent is propylene.

In this embodiment, reactor 20 comprises three alkylation reaction zones 31, 32 and 33. First alkylation reaction zone 31 contains two alkylation catalyst beds 211 and 212, second alkylation reaction zone 32 contains two alkylation catalyst beds 213 and 214, and third alkylation reaction zone 33 contains two alkylation catalyst beds 215 and 216. Coolers (or heat exchangers) 22 are contained in reactor 20 between every two of alkylation reaction zones 31, 32 and 33. Each alkylation catalyst bed 211, 212, 213, 214, 215, and 216 may comprise the same or different alkylation catalysts.

During the alkylation process, fresh benzene 11, after passing through a drying column (not shown) to reduce its water content, through treaters (not shown) to remove most catalyst poisons, such as nitrogen and sulfur containing organic species, and through a heat exchanger (not shown) to raise its temperature, is fed to a first alkylation reaction zone 31 via the uppermost alkylation catalyst bed 211, which also receives fresh propylene 12. After alkylation reaction in alkylation catalyst bed 211, an effluent is withdrawn from alkylation catalyst bed 211 and then flows down into alkylation catalyst bed 212 of first alkylation reaction zone 31. Alkylation catalyst bed 212 also receives fresh propylene 12. Each of alkylation catalyst beds 211 and 212 of first alkylation reaction zone 31 typically operates at or near 100% propylene conversion, but may operate at lower conversions so that a first effluent output from the alkylation catalyst bed 212, i.e., from first alkylation reaction zone 31, mainly comprise cumene, unreacted benzene and small amount of byproducts.

A portion of first effluent 132 is then passed through a cooler 22 for indirect heat exchanges so as to cool the effluent to a temperature above, similar or below to the temperature of fresh benzene 11. The cooled portion 132 and the un-cooled portion 131 are both injected into a region between catalyst bed 212 of the first alkylation reaction zone 31 and the alkylation catalyst bed 213 of the first alkylation reaction zone 32, wherein such region also receives fresh propylene 12. After the alkylation reaction in the alkylation catalyst bed 213, an effluent is withdrawn from alkylation catalyst bed 213. This effluent then flows down into the alkylation catalyst bed 214 of the second alkylation reaction zone 32 along with additional fresh propylene 12. Each of alkylation catalyst beds 213 and 214 of second alkylation reaction zone 32 typically operates at or near 100% propylene conversion, but may operate at lower conversions so that the second effluent output from alkylation catalyst bed 214, i.e., from second alkylation reaction zone 32, mainly comprises cumene, unreacted benzene and small amount of byproducts.

A portion of second effluent 142 is then passed through a cooler 22 for indirect heat exchanges so as to cool the effluent to a temperature above, similar or below to the temperature of fresh benzene 11. Cooled portion 142 and un-cooled portion 141 are both injected into a region between catalyst bed 214 of the second alkylation reaction zone 32 and the alkylation catalyst bed 215 of the third alkylation reaction zone 33, wherein said region also receives additional fresh propylene 12. After the alkylation reaction in the alkylation catalyst bed 215, an effluent is withdrawn and output from alkylation catalyst bed 215 and then flows down into the alkylation catalyst bed 216 of third alkylation reaction zone 33 along with additional fresh propylene 12. Similarly, each of alkylation catalyst beds 215 and 216 of third alkylation reaction zone 33 typically operates at or near 100% propylene conversion, but may operate at lower conversions so that the third effluent output from alkylation catalyst bed 216, i.e., from third alkylation reaction zone 33 mainly comprising cumene, unreacted benzene and small amounts of byproducts. In this embodiment, third alkylation reaction zone 33 is a finishing alkylation reaction zone of reactor 20, accordingly the third effluent is the reactor effluent output from reactor 20.

The reactor effluent can then be divided into two streams 151 and 152. Stream 151 can pass into separators 23 and 24 so as to serially separate the unreacted benzenes 16, the desired cumene 18, and polyisopropylbenzene 19, including diisopropylbenzene and tri-isopropylbenzene. The unreacted benzenes 16 can be recycled to be combined with the fresh benzene 11. The polyisopropylbenzene can be supplied to a transalkylation reactor (not shown) for further production of cumene by transalkylation of polyisopropylbenzene with additional benzene. Stream 152 can be passed through a cooler 22 and then recycled into reactor 20 or other downstream/upstream reactor for further alkylation of the unreacted benzene. In any embodiments of present inventions, the recycle ratio of reactor effluent is less than five, that is, the weight of stream 152 is less than five times the weight of stream 151.

In an alternative embodiment, the recycle ratio of reactor effluent can be zero. That is, none of reactor effluent is recycled and the reactor effluent is not divided. In FIG. 4, the reactor effluent is stream 151 and none of the reactor effluent is recycled as stream 152.

In some embodiments this disclosure relates to:

Paragraph 1. A process for production of a monoalkyl aromatic compound in a reactor having at least a first and a second series-connected alkylation reaction zones, each reaction zone having an alkylation catalyst, the process comprising the steps of:

a) introducing a first feed comprising an alkylatable aromatic compound and a second feed comprising an alkylating agent into said first alkylation reaction zone;

b) operating said first alkylation reaction zone under at least partly liquid phase conditions sufficient to cause alkylation of said alkylatable aromatic compound by said alkylating agent in the presence of said alkylation catalyst to produce a first effluent comprising said monoalkyl aromatic compound and unreacted alkylatable aromatic compound;

c) withdrawing said first effluent from said first reaction zone;

d) cooling at least a portion of said first effluent to form a cooled first effluent;

e) supplying said cooled first effluent and the rest of said first effluent, and optionally a third feed comprising additional said alkylating agent to said second alkylation reaction zone; and f) operating said second alkylation reaction zone under at least partly liquid phase conditions sufficient to cause alkylation of said unreacted alkylatable aromatic compound by said alkylating agent in the presence of said alkylation catalyst to produce a second effluent comprising additional said monoalkyl aromatic compound and unreacted alkylatable aromatic compound.

Paragraph 2. The process of Paragraph 1, wherein said step d) comprises cooling of said first effluent.

Paragraph 3. The process of Paragraph 1, wherein said step d) comprises cooling all of said first effluent, and step (e) comprises supplying all of said cooled first effluent to said second alkylation reaction zone.

Paragraph 4. The process of any of Paragraphs 1 to 3, wherein said first and said second alkylation reaction zone each independently comprises at least one alkylation catalyst bed having said alkylation catalyst.

Paragraph 5. The process of any of Paragraphs 1 to 3, wherein each of said first and said second alkylation reaction zones independently comprises one, two, three, or four series-connected alkylation catalyst beds having said alkylation catalyst.

Paragraph 6. The process of any of Paragraphs 1 to 5, wherein said alkylation catalyst comprises at least one of zeolite beta, faujasite, mordenite, TEA-mordenite, zeolite Y, Ultrastable Y (USY), Dealuminzed Y (Deal Y), Rare earth exchanged Y (REY), Ultrahydrophobic Y (YHP-Y), or a combination thereof.

Paragraph 7. The process of any of Paragraphs 1 to 5, wherein said alkylation catalyst comprises a MCM-22 family material.

Paragraph 8. The process of Paragraph 7, wherein said MCM-22 family material is characterized by an X-ray diffraction pattern including d-spacing maxima at 12.4±0.25, 6.9±0.15, 3.57±0.07 and 3.42±0.07 Angstrom.

Paragraph 9. The process of any of Paragraphs 1 to 5, wherein said alkylation catalyst comprises at least one of molecular sieves MCM-22, MCM-36, MCM-19, MCM-56, or a combination thereof.

Paragraph 10. The process of any of Paragraphs 1 to 5, wherein said alkylation catalyst comprises at least one of UZM-8, UZM-HS, and mixtures thereof.

Paragraph 11. The process of any of Paragraphs 1 to 10, wherein said conditions are such that said steps b) or f), or both, having a ratio of the volume of vapor to the sum of vapor and liquid from about 0.01 to about 0.1.

Paragraph 12. The process of any of Paragraphs 1 to 10, wherein said conditions are such that said steps b) or f) or bath, are maintained in the liquid phase.

Paragraph 13. The process of any of Paragraphs 1 to 12 further comprising the steps of:

g) withdrawing a reactor effluent which comprises at least said first and second effluents from said reactor; and h) recycling a portion of said effluent to said first reaction zone or said second reaction zone for alkylation of said unreacted alkylatable aromatic compound, wherein the ratio by weight of said recycled portion to the non-recycled portion of said reactor effluent is in the range of greater than or equal to about zero to less than or equal to about 5.

Paragraph 14. The process of Paragraph 13, wherein said ratio of step h) is in the range of greater than or equal to about zero to less than 2.5.

Paragraph 15. The process of any of Paragraphs 1 to 14, wherein said alkylating agent comprises an alkene.

Paragraph 16. The process of Paragraph 15, wherein said alkene comprises ethylene, propylene, or butene.

Paragraph 17. The process of any of Paragraphs 1 to 16, wherein said alkylating agent comprises ethylene, said alkylatable aromatic compound comprises benzene, and said monoalkyl aromatic compound comprises ethylbenzene.

Paragraph 18. The process of Paragraph 17, wherein said conditions in the steps b) and f), or both, comprise a temperature of about 120° C. to about 270° C., and a pressure of about 675 KPa to about 8300 KPa.

Paragraph 19. The process of any of Paragraphs 1 to 16, wherein said alkylating agent comprises propylene, said alkylatable aromatic compound comprises benzene, and said monoalkyl aromatic compound comprises cumene.

Paragraph 20. The process of Paragraph 19, wherein said conditions in the steps b) and f), or bath, comprise a temperature of about 75° C. to about 250° C., and a pressure of about 675 kPa to about 5000 kPa.

Paragraph 21. The process of any of Paragraphs 1 to 16, wherein said alkylating agent comprises 1-butene and/or 2-butene, said alkylatable aromatic compound comprises benzene and said monoalkyl aromatic compound comprises sec-butylbenzene.

Paragraph 22. The process of Paragraph 21, wherein said conditions in the steps b) and f) or both, comprise a temperature of about 75° C. to about 250° C., and a pressure of about 355 kPa to about 4000 kPa.

Paragraph 23. A reactor for production of a monoalkyl aromatic compound by alkylating an alkylatable aromatic compound with an alkylating agent comprising:

a) at least a first and a second alkylation reaction zones; and b) a cooler disposed between said first and second alkylation reaction zone.

Paragraph 24. The reactor of Paragraph 23, wherein said first and second alkylation reaction zone each independently comprise at least one alkylation catalyst bed.

Paragraph 25. The reactor of any of Paragraphs 23 to 24, said first and second alkylation reaction zones each independently comprises one, two, three, or four series-connected alkylation catalyst beds.

Paragraph 26. A process for production of cumene in a reactor having at least a first and a second series-connected alkylation reaction zones, each reaction zone having an alkylation catalyst, the process comprising the steps of:

a) introducing a first feed comprising benzene, and a second feed comprising propylene into said first alkylation reaction zone;

b) operating said first alkylation reaction zone under liquid phase conditions sufficient to cause alkylation of said benzene by said propylene in the presence of said alkylation catalyst to produce a first effluent comprising said cumene and unreacted benzene;

c) withdrawing said first effluent from said first reaction zone;

d) cooling at least a portion of said first effluent to form a cooled first effluent;

e) supplying said cooled portion and the rest of said first effluent, and a third feed comprising additional propylene to said second alkylation reaction zone;

f) operating said second alkylation reaction zone under liquid phase conditions sufficient to cause alkylation of said unreacted benzene by said additional propylene in the presence of said alkylation catalyst to produce a second effluent comprising additional said cumene and unreacted benzene;

g) withdrawing a reactor effluent which comprises at least said first and second effluents from said reactor; and h) recycling a portion of said reactor effluent to said first alkylation reaction zone or said second alkylation reaction zone for alkylation of said unreacted benzene, wherein the ratio by weight of said recycled portion to the non-recycled portion of said reactor effluent is in the range of greater than or equal to zero to less than or equal to about 5.

Paragraph 27. A reactor adapted to a process for production of cumene comprising:

a) a reactor having an inlet, an outlet and at least a first and a second series-connected alkylation reaction zones, wherein each reaction zone having alkylation catalyst, said inlet adapted to introduce a first feed comprising benzene and a second feed comprising propylene into said first alkylation reaction zone, said first alkylation reaction zone operated under liquid phase conditions sufficient to cause alkylation of said benzene by said propylene in the presence of said alkylation catalyst to produce a first effluent comprising said cumene and unreacted benzene, said outlet adapted to withdraw said first effluent from said first reaction zone;

b) a cooler disposed between said first and second alkylation reaction zones and adapted to cool at least a portion of said first effluent to form a cooled first effluent, wherein said cooled portion, the rest of said first effluent, and a third feed comprising additional propylene is supplied to said second alkylation reaction zone, said second alkylation reaction zone under liquid phase conditions sufficient to cause alkylation of said unreacted benzene by said additional propylene in the presence of said alkylation catalyst to produce a second effluent comprising additional said cumene and unreacted benzene, wherein a reactor effluent which comprises at least said first and second effluents from said reactor is withdrawn from said outlet, and wherein a portion of said reactor effluent is recycled to said first alkylation reaction zone or said second alkylation reaction zone for alkylation of said unreacted benzene, wherein the ratio by weight of said recycled portion to the non-recycled portion of said reactor effluent is in the range of greater than or equal to zero to less than or equal to about 5.

Paragraph 28. The reactor of Paragraph 27, wherein said first and second alkylation reaction zones each independently comprise at least one alkylation catalyst bed.

Paragraph 29. The reactor of Paragraph 28, wherein said first and second alkylation reaction zones each independently comprises one, two, three, or four series-connected alkylation catalyst beds.

All patents, patent applications, test procedures, priority documents, articles, publications, manuals, and other documents cited herein are fully incorporated by reference for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the invention pertains.

The invention claimed is:

1. A process for production of cumene comprising the steps of:

(a) introducing a first feed comprising benzene and a second feed comprising propylene into a reactor having at least a first and a second series-connected alkylation reaction zone, each reaction zone having an alkylation catalyst, wherein said alkylation catalyst comprises at least one of zeolite beta, faujasite, mordenite, TEA-mordenite, zeolite Y, Ultrastable Y (USY), Dealuminized Y (Deal Y), Rare earth exchanged Y (REY), Ultrahydrophobic Y (UHP-Y), MCM-22, MCM-36, MCM-49, MCM-56 or a combination thereof;

(b) operating said first alkylation reaction zone under liquid phase conditions sufficient to cause alkylation of said benzene by said propylene in the presence of said alkylation catalyst to produce a first effluent comprising said cumene and unreacted benzene;

(c) withdrawing said first effluent from said first reaction zone;

(d) cooling at least a portion of said first effluent to form a cooled first effluent;

(e) supplying said cooled portion and the rest of said first effluent, and a third feed comprising additional propylene to said second alkylation reaction zone;

(f) operating said second alkylation reaction zone under liquid phase conditions sufficient to cause alkylation of said unreacted benzene by said additional propylene in the presence of said alkylation catalyst to produce a second effluent comprising additional said cumene and unreacted benzene, wherein said first alkylation catalyst has a greater number of acid sites per unit mass of catalyst than said second alkylation catalyst;

(g) withdrawing a reactor effluent which comprises at least said first and second effluents from said reactor; and (h) recycling a portion of said reactor effluent to said first alkylation reaction zone or said second alkylation reaction zone for alkylation of said unreacted alkylatable aromatic compound, wherein the ratio by weight of said recycled portion to the non-recycled portion of said reactor effluent is in the range from greater than zero to about 1.

2. The process of claim 1, wherein said step d) comprises cooling at least 50% by weight of said first effluent.

3. The process of claim 1, wherein said step d) comprises cooling all of said first effluent, and step (e) comprises supplying all of said cooled first effluent to said second alkylation reaction zone.

4. The process of claim 1, wherein said first and said second alkylation reaction zone each independently comprises at least one alkylation catalyst bed having said alkylation catalyst.

5. The process of claim 1, wherein each of said first and said second alkylation reaction zones independently comprises one, two, three, or four series-connected alkylation catalyst beds having said alkylation catalyst.

6. The process of claim 1, wherein said conditions are such that said steps b) or f) or both having a ratio of the volume of vapor to the sum of vapor and liquid from about 0.01 to about 0.1.

7. The process of claim 1, wherein said conditions are such that said steps b) or f) or both are maintained in the liquid phase.

8. The process of claim 1, wherein said conditions in steps b) and f), or both, comprise a temperature of about 75° C. to about 250° C. and a pressure of about 675 kPa to about 5000 kPa.

* * * * *

UNITED STATES PATENT AND TRADEMARK OFFICE
CERTIFICATE OF CORRECTION

PATENT NO. : 9,902,664 B2
APPLICATION NO. : 14/372095
DATED : February 27, 2018
INVENTOR(S) : Matthew J. Vincent et al.

Page 1 of 1

It is certified that error appears in the above-identified patent and that said Letters Patent is hereby corrected as shown below:

Column 18, Lines 53 to Line 60, cancel the text of Claim 1, step (f), and in its place insert the following:
--(f) operating said second alkylation reaction zone under liquid phase conditions sufficient to cause alkylation of said unreacted benzene by said additional propylene in the presence of said alkylation catalyst to produce a second effluent comprising additional said cumene and unreacted benzene, wherein said alkylation catalyst in said first series-connected alkylation reaction zone has a greater number of acid sites per unit mass of catalyst than said alkylation catalyst in said second series-connected alkylation reaction zone;--

Signed and Sealed this
Twenty-sixth Day of June, 2018

Andrei Iancu
*Director of the United States Patent and Trademark Office*